United States Patent [19]

Kronner

[11] Patent Number: 4,917,679
[45] Date of Patent: Apr. 17, 1990

[54] SYRINGE WITH PROTECTIVE SLEEVE

[76] Inventor: Richard F. Kronner, 1443 Upper Cleveland Rapids Rd., Roseburg, Oreg. 97479

[21] Appl. No.: 243,291

[22] Filed: Sep. 12, 1988

[51] Int. Cl.⁴ .............................................. A61M 5/32
[52] U.S. Cl. .................................... 604/198; 128/763; 604/263
[58] Field of Search ............... 604/192, 198, 263, 110; 128/763–766

[56] References Cited

U.S. PATENT DOCUMENTS

| | | | |
|---|---|---|---|
| 4,425,120 | 1/1984 | Sampson et al. | 604/198 |
| 4,695,274 | 9/1987 | Fox | 604/198 |
| 4,743,233 | 5/1988 | Schneider | 604/198 X |
| 4,747,831 | 5/1988 | Kulli | 604/110 |

OTHER PUBLICATIONS

Copy of an article describing a "peachcapp".

Primary Examiner—Dalton L. Truluck
Attorney, Agent, or Firm—Kolisch, Hartwell & Dickinson

[57] ABSTRACT

The combination of a syringe which includes a barrel and a needle projecting from one end of the barrel, and a protector slidably mounted on the syringe barrel. A guard portion in the protector shields the tip of the needle with the protector relatively fully extended on the barrel, and in this position a seal inside the protector seals the tip of the needle. The needle is exposed with the protector in a relatively fully retracted position. In an intermediate position, the needle is shielded but the tip is not sealed.

10 Claims, 2 Drawing Sheets

SYRINGE WITH PROTECTIVE SLEEVE

BACKGROUND AND SUMMARY OF THE INVENTION

This invention relates to what is referred to herein as a protector incorporable with a syringe, the projector being adjustable to inhibit accidental puncturing of one using the syringe with the needle of the syringe. More specifically, it concerns a syringe and protector combination where the protector also includes a sealing member which seals the tip of the syringe needle with the protector having a selected position on the syringe, so as to inhibit exposure of the contents of the syringe to oxygen in the air. An additional feature is a construction whereby the protector may be used in coupling the syringe to an analyzer probe, as a preliminary to transferring liquid in the syringe to the analyzer for the purpose of analyzing the content of the liquid.

Technicians who draw a fluid, such as blood, from a patient, or use a syringe with needle for the injection of material into a patient, are subject to personal injury after the needle in the syringe is withdrawn from the patient through accidental puncturing with the now possibly contaminated needle. Presently many syringes are supplied with a protective needle cover, which essentially covers only the needle in the syringe, and the needle is often recovered with this needle cover after use of the syringe because of the difficulty of using safer techniques at the patient's bedside. This procedure also potentially exposes the technician to potential puncture from the possibly contaminated needle.

So-called blood gas analyzers are known which in use are loaded with a sample of blood, with the analyzer then producing determinations indicative of oxygen and carbon dioxide level in the blood. In using such an analyzer, arterial blood is withdrawn from a patient into a syringe and it is frequently necessary to remove the possibly contaminated needle from the syringe prior to placing the barrel of the syringe against a port in the analyzer for the purpose of loading the analyzer with the blood sample. With this procedure, contaminated blood is susceptible to being splattered on the technician's body.

It is necessary to keep any blood sample which is to be analyzed with a blood gas analyzer free from exposure to air and the oxygen within the air, because one of the purposes of the assay made is to test for oxygen content and any exposure to oxygen in the air may alter the sample. Additionally, it may be desirable to save a portion of a blood sample for later loading into an analyzer in the event that the first assay is not correct, again requiring that the sample obtained not be exposed to oxygen.

The need to protect technicians from diseases such as hepatitis and AIDS makes the problems above discussed in connection with possible contamination by a patient's blood particularly important.

The protector of this invention addresses the above discussed problems and requirements in a highly practical and satisfactory manner. Among the functions permitted by the device of the invention is the ability for a technician relatively easily to shield or cover a needle after such has been inserted into a patient, with substantially no exposure to possible puncturing by the needle of the syringe. The covering operation may be performed using only one hand by the technician, and the operation may be performed immediately after the withdrawing of a syringe needle from a patient. The protector preferably includes a needle tip sealing member, which functions to seal the tip of the syringe needle with the protector in a selected position. The protector further is provided with a construction which enables it to be fitted against a blood gas analyzer, more particularly, a probe in the analyzer, to effect transfer of blood from the syringe to the analyzer. In this procedure, again the needle of the syringe is covered so as to inhibit accidental puncturing of someone handling the syringe.

BRIEF DESCRIPTION OF THE DRAWINGS

These and various objects and advantages are attained by the invention, which is described hereinbelow in conjunction with the accompanying drawings, wherein.

DETAILED DESCRIPTION OF A PREFERRED EMBODIMENT

Figure 6:
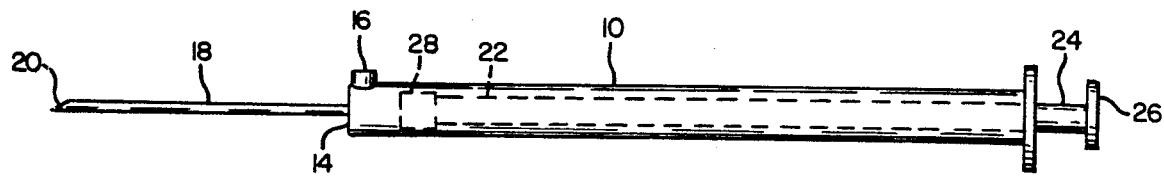
FIG. 6 illustrates a syringe with the protector removed.

Referring now to the drawings, the device illustrated includes an elongate syringe barrel 10, which normally may be made of a transparent or semitransparent plastic, which enables a technician to see blood entering the syringe barrel as when withdrawing a sample from a patient. Joined to the barrel at one end is a flange 12 engaged by the fingers of a technician when using the syringe, more particularly, as when depressing a plunger (to be described) to shift it axially along the length of the syringe barrel. The left end of the syringe barrel, as shown in FIG. 6, is essentially closed by a closure element 14 mounted on the barrel so that the barrel and element are an integral structure. A radially extending positioning pin or detent 16 is an integral part of the barrel.

Suitably mounted in closure element 14 is an elongate needle 18. The needle, as is conventional, is hollow, and the interior of the needle communicates with the interior of barrel 10. The outer or exposed end of the needle is provided with a sharpened end or tip, shown at 20.

Mounted for reciprocation within barrel 10 is a plunger 22. The plunger includes a shank 24 which extends outwardly from the end of the syringe barrel which is opposite the end having needle 18, the shank terminating in a depressor portion 26. The end of the plunger opposite the end having portion 26 is provided with a head portion 28 which, as is conventional, slides along the interior of the syringe barrel. The head portion is vented and contains material which swells when in contact with blood to form a seal.

Figure 4:
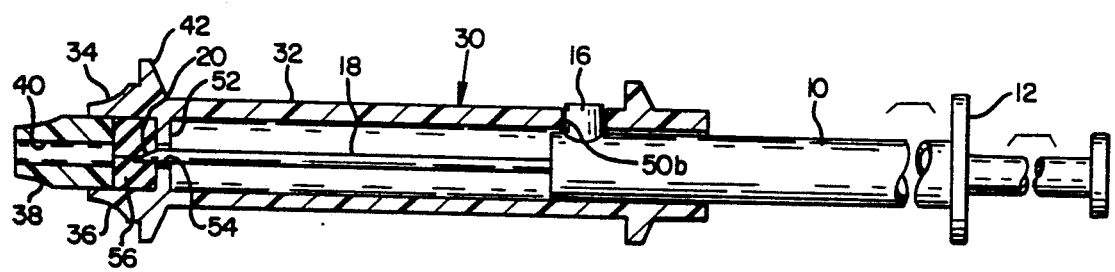
FIG. 4 is a side view, partially in section, showing the protector occupying a fully extended position on the syringe.
Figure 5:
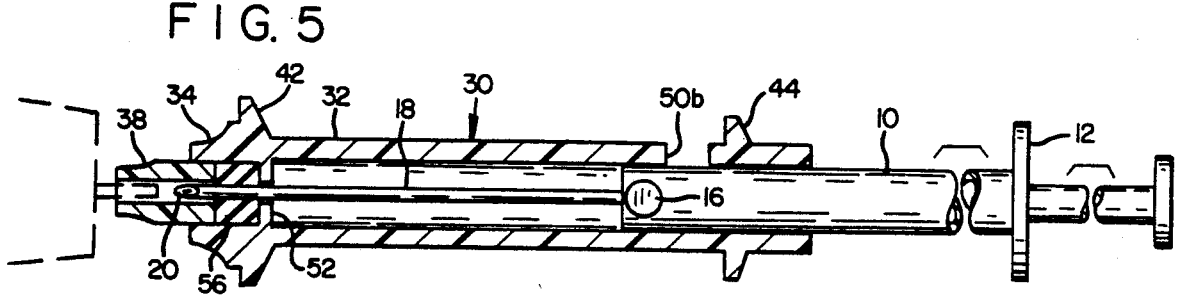
FIG. 5 is a view, similar to FIG. 4, but illustrating another position of the protector on the syringe, which adapts the assembly for fitting against an analyzer probe in a blood gas analyzer.

Encompassing the barrel of the syringe and mounted for axial movement therealong is a protector or protective sleeve 30 (see FIGS. 4 and 5). Describing with more particularity this protective sleeve, such includes an elongate sleeve body 32 with an inner circumference slightly greater than the outer circumference of the syringe barrel so that the sleeve body may slide easily along the length of the syringe barrel, as well as be relatively rotated with respect to the syringe barrel. The rear end of the sleeve body, i.e., the end which is facing flange 12, is open to permit the barrel to extend therethrough. Its opposite end, or forward end, is essentially closed by closure portion 34, which on the outside tapers over a region 36 to joinder with a tubular segment 38. The interior of the tubular segment has a passage 40 accommodating movement therethrough of syringe needle 18 with relative movement of the protective sleeve along the syringe barrel.

To facilitate manipulation of the protective sleeve on the syringe barrel and use of the syringe when withdrawing a blood sample, the exterior of the sleeve body may be provided, adjacent its opposite ends, with circumferential flanges 42, 44 and raised ridges (see FIG. 3A), shown at 46, 48, extending axially on the sleeve body.

The protective sleeve illustrated is guided for movement along the syringe barrel between predefined positions. Further explaining (see FIG. 2), extending along the sleeve body is an elongate slot having a straight extent 50, which, for the most part, substantially parallels the axis of the sleeve body. Slot 50 terminates adjacent the forward end of the slot in a leg portion 50a extending transversely of extent 50. The opposite end of the slot terminates in an offset transversely extending leg 50b. Leg 50b joins with a small segment 50c extending in an axial direction. Adjacent leg 50b, the slot has a constriction 50d (see FIG. 2).

Figure 1:
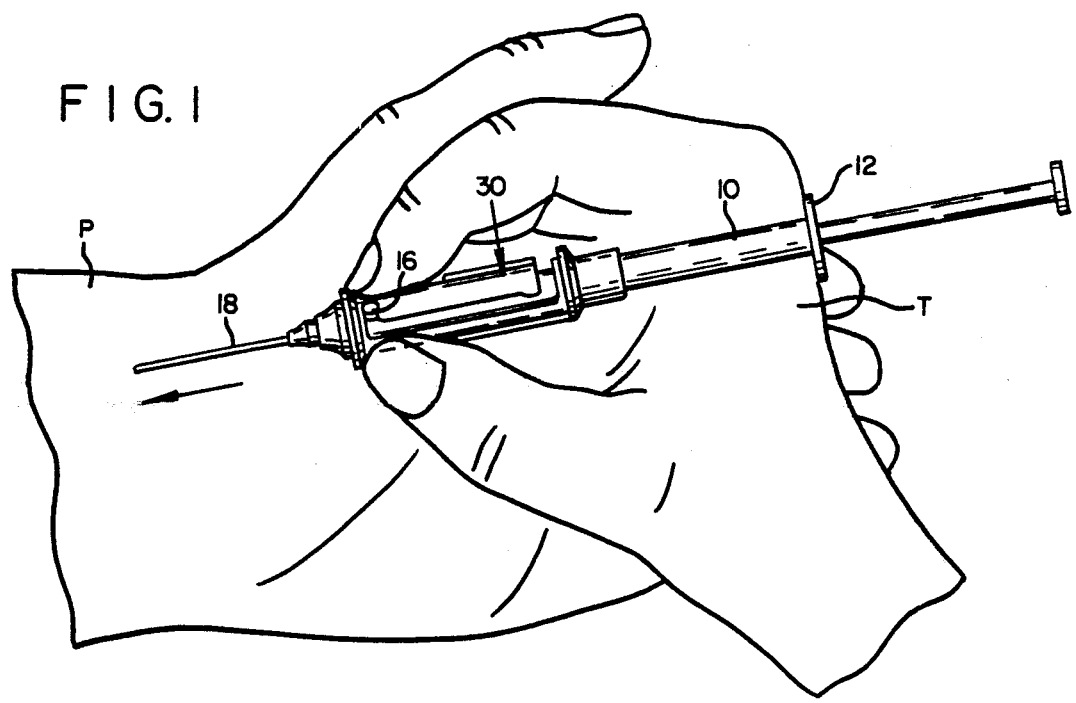
FIG. 1 is a side view of a syringe and protector assembly as contemplated by the invention, and showing in simplified outline how such is manipulated in puncturing an artery for the purpose of withdrawing a blood sample.

With the protective sleeve mounted on the syringe body, pin 16 rides within the slot 50. With the protective sleeve fully retracted on the syringe barrel and pin 16 located in leg 50a, as shown in FIG. 1, the protective sleeve is prevented from moving to an extended position, but can only relatively rotate with respect to the syringe barrel. Positioning of the pin within straight extent 50 of the slot permits the protective sleeve to move from its fully retracted to a fully extended position, determined by the pin moving past constriction 50d and into alignment with leg 50b. With the pin so positioned, the protective sleeve may be rotated to move the pin behind segment 50c. The sleeve is then movable axially to place the pin at the end of this segment, this sleeve movement being slightly rearwardly on the barrel and effective to place the sleeve in what is referred to herein as an intermediate position.

As can be seen with reference to FIGS. 4 and 5 showing the interior of the forward end of the protective sleeve, an internal web 52 forms part of the sleeve, having a center passage 54. The web becomes located directly adjacent the end of the syringe barrel with the protective sleeve fully retracted. Between web 52 and the inner end of tubular segment 38 is an elastomer insert 56, which functions as a sealing member. With the protective sleeve in its fully extended position as shown in FIG. 4, needle 18 passes through passage 54 (thus to be centered by the passage) to have its tip or sharpened end buried in insert 56. The interior passage of the needle then is sealed by the insert.

With movement of the sleeve to shift the pin along leg 50b and thence into segment 50c, the protective sleeve may be shifted rearwardly slightly from a fully extended position to an intermediate position, which is the discharge position. This places the tip of the needle slightly forwardly and beyond insert 56, as shown in FIG. 5, with the interior of the needle now being exposed to the interior of segment 38.

Describing now how the device may be utilized, the device may be packaged for distribution with the protective sleeve in its fully retracted position and with the usual removable needle cover covering the now exposed syringe needle. To obtain a blood sample, the technician removes the protective cover and positions the device with his hand T, as shown in FIG. 1, gripping the the device adjacent its forward end between the thumb and forefinger. The needle is inserted into the artery of the patient, shown as P. With insertion of the needle, blood enters into the needle and the syringe barrel and the technician is able to observe the passing of blood as it enters the syringe barrel by observing that part of the syringe barrel exposed by slot 50.

Figure 2:
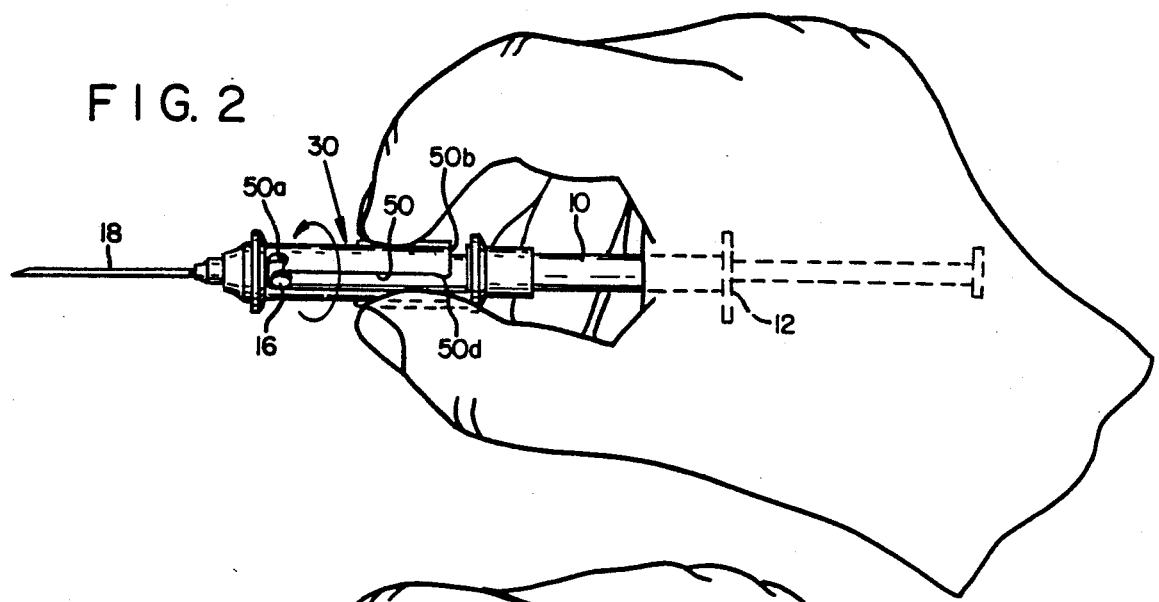
FIG. 2 is another side view of the syringe, showing how a protector on the syringe barrel is rotated prior to actual shifting the protector in a direction producing shielding of the syringe needle.
Figure 3:
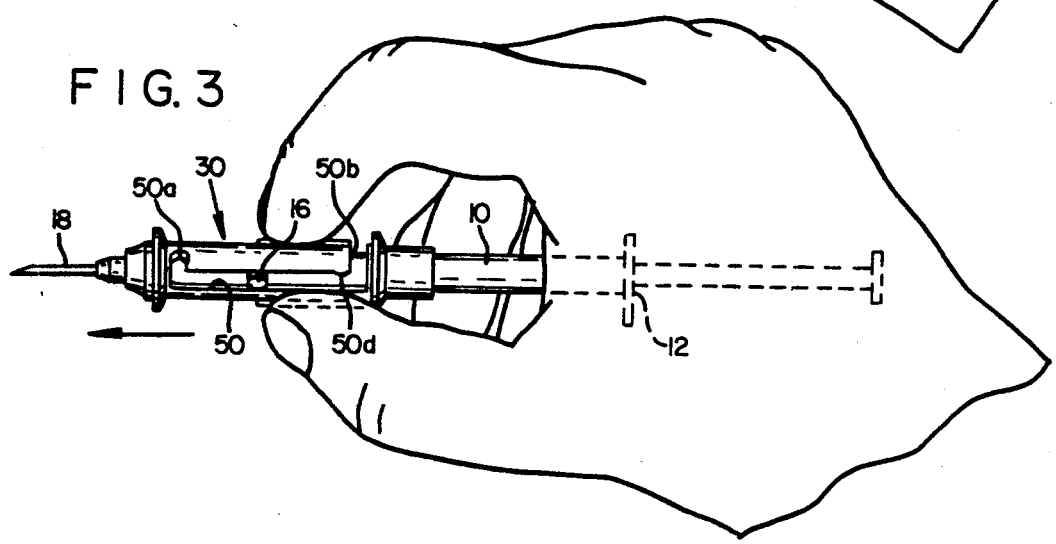
FIG. 3. illustrates the protector being shifted to a shielding position.

With the blood sample obtained, the technician, and as shown in FIG. 2, first pulls the device outwardly to free the needle, and with the free hand, places a cotton swab or other medium against the puncture wound. With the thumb and forefinger of the hand which grips the device, the operator rotates the protective sleeve to move pin 16 into alignment with lineal extent 50 of the slot (see FIG. 2). The barrel may be held with such against the palm and steadied by the third finger of the hand. It is then a relatively simple matter, and with the thumb and forefinger, to shift the sleeve toward its fully extended position, as shown in FIG. 3. In this fully extended position, which is the transport position, the needle is completely covered and the tip of the needle is sealed by the sealing member earlier described. The snap-action of constriction 50d locks the syringe in place. The syringe may be set aside to free both operator hands for other care requirements, dressing applications, etc. Leakage from the needle is prevented by the seal. Air is prevented from entering through the needle.

Figure 3A:
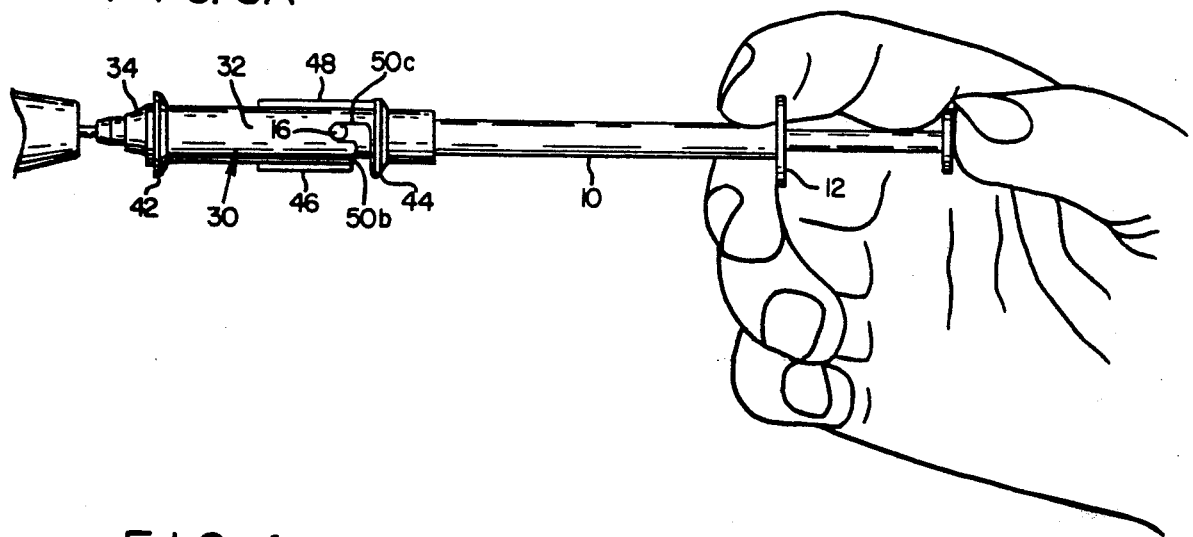
FIG. 3A illustrates the protector and syringe fitted onto the probe of a blood gas analyzer.

To load an analyzer probe with the contents of the syringe, the sleeve is rotated and shifted axially to the extent permitted by segment 50c of the slot. This leaves the tip of the needle still covered by the protector, but with such located beyond the rubber or elastomer insert 56. The probe of the analyzer may be fitted onto tubular segment 38, and the blood sample loaded into the analyzer with depressing of the plunger, as shown in FIG. 3A.

If desired, the device may be manufactured with a second transversely extending slot segment, located approximately midway between the ends of the slot 50. With the pin 16 positioned within this segment, the needle would be positioned to have only partial extension from the protective sleeve. The syringe and protective sleeve could then be used for radial artery (short needle) and for femoral artery (long needle) sampling.

The device has been described in connection with obtaining a blood sample from a patient. Other uses are possible. For instance, the device may be used for partial injection into a patient of certain material with the protective sleeve adjusted to provide covering of the syringe needle after making such partial injection, the protective sleeve being subsequently adjustable to expose the needle for the remainder of the injection.

While a particular embodiment of the invention has been described, it should be obvious that variations and modifications are possible without departing from the invention.

It is claimed and desired to secure by Letters Patent:

1. In combination with a syringe including a barrel and an elongate needle projecting from one end of the barrel, the needle terminating in a tip:

a needle protector having an end portion slidably mounted on the barrel and an opposite end portion, said opposite end portion having a passage extending therethrough and said protector having one position on the barrel where the needle extends through said passage with the needle exposed beyond said opposite end portion, said protector with movement thereof along the barrel in a direction extending away from the end of the barrel having the needle being shiftable to a needle guard position where the tip of the needle is located inwardly of said opposite end portion of the protector, and guide structure interposed between the protector and said syringe defining said one and said guard positions, said protector further including a flexible sealing member adjacent said passage constructed to seal the tip of a needle with the protector in said guard position.

2. The combination of claim 1, wherein said opposite end portion of the protector terminates in a tubular segment having said passage, the tubular segment having an exposed outer end adapted for fitting on an analyzer probe, said flexible sealing member being disposed interiorly of the protector inwardly of the exposed outer end of the tubular segment.

3. The combination of claim 2, which includes means operatively interposed between the barrel of the syringe and the protector defining said one and said guard position, said means further defining a third position of the protector relative to the barrel of the syringe where the tip of the needle is disposed beyond the flexible sealing member but inwardly of the extremity of said exposed outer end of the tubular segment.

4. In combination with a syringe, including a barrel and needle projecting from one end of the barrel terminating in a tip:

an elongate sleeve encompassing the barrel and mounted for sliding movement therealong, travel-defining means interposed between the barrel and sleeve defining at least three positions for the sleeve relative to the barrel, one position being a relatively fully retracted position, another position being a relatively fully extended position, and a third position being an position intermediate the relatively fully extended and the relatively fully retracted positions, said sleeve having a needle guard portion at one end thereof which the needle passes through with the sleeve in its relatively fully retracted position, the tip of the needle being located beyond the guard portion with the sleeve in said fully retracted position, the tip of the needle being located within the sleeve with the sleeve in said extended position and said intermediate position, and a seal within the sleeve sealing the tip of the needle with the sleeve in its said extended position, the needle projecting beyond said seal with the sleeve in its said intermediate position.

5. The combination of claim 3, wherein said travel-defining means comprises a slot extending along the sleeve and a detent integral with the barrel, the slot being configured to resist axial movement of the sleeve on the barrel with the sleeve in its relatively fully retracted position.

6. The combination of claim 5, wherein said slot is configured to restrict movement of the sleeve axially on the barrel with the sleeve in its relatively fully extended position.

7. The combination of claim 4, wherein said travel-defining means comprises a slot extending longitudinally of the sleeve to permit movement of the sleeve between its said fully extended and fully retracted positions and said slot includes an offset portion which the detent may travel into with the sleeve in its relatively fully extended position restricting axial movement of the sleeve relative to the barrel.

8. The combination of claim 7, wherein the slot has a snap-acting constriction which the detent travels through with the sleeve shifted to its relatively fully extended position.

9. The combination of claim 4, wherein said guard portion includes a tubular segment terminating the guard portion having an exposed outer end, the needle passing through the interior of the tubular segment with shifting of the sleeve from its relatively fully extended to its relatively fully retracted position, and wherein said seal comprises an elastomer element disposed within the sleeve inwardly of the tubular segment and positioned to encompass the tip of the needle with the sleeve in its extended position.

10. The combination of claim 9, wherein said tubular segment is constructed to be fitted on an analyzer probe.

* * * * *